(12) United States Patent
Shirai et al.

(10) Patent No.: US 6,194,693 B1
(45) Date of Patent: Feb. 27, 2001

(54) GAS SENSOR WITH CERAMIC HEATER

(75) Inventors: Makoto Shirai; Hisao Kuroki; Masayuki Kobayashi, all of Kuwana (JP)

(73) Assignee: DENSO Corporation, Kariya (JP)

( * ) Notice: Subject to any disclaimer, the term of this patent is extended or adjusted under 35 U.S.C. 154(b) by 0 days.

(21) Appl. No.: 09/365,173

(22) Filed: Aug. 2, 1999

(30) Foreign Application Priority Data

| Jan. 14, 1999 | (JP) | 11-008185 |
| Apr. 27, 1999 | (JP) | 11-120248 |
| Aug. 3, 1999 | (JP) | 10-219031 |

(51) Int. Cl.[7] .................................................. H05B 3/10
(52) U.S. Cl. ........................ 219/552; 219/543; 219/548
(58) Field of Search .................................. 219/260, 267, 219/270, 520–523, 538, 541, 544, 548; 428/446

(56) References Cited

U.S. PATENT DOCUMENTS

| 4,357,526 | * 11/1982 | Yamamoto et al. | 219/544 |
| 4,486,651 | * 12/1984 | Atsumi et al. | 219/553 |
| 4,636,293 |   1/1987  | Bayha et al. | 204/428 |
| 4,733,056 | *  3/1988 | Kojima et al. | 219/543 |
| 4,824,550 |   4/1989  | Ker et al. | 204/427 |
| 5,233,166 | *  8/1993 | Maeda et al. | 219/552 |
| 5,264,681 | * 11/1993 | Nozaki et al. | 219/544 |
| 5,560,851 | * 10/1996 | Thimm et al. | 219/543 |
| 5,756,215 | *  5/1998 | Sawamura et al. | 428/446 |
| 5,804,796 | *  9/1998 | Kanesaka | 219/263 |

FOREIGN PATENT DOCUMENTS 5-2101    1/1993  (JP).

* cited by examiner

Primary Examiner—Tu Ba Hoang
(74) Attorney, Agent, or Firm—Pillsbury Madison & Sutr

(57) ABSTRACT

A ceramic heater that may be used in an oxygen sensor for automotive air-fuel ratio control systems and includes a ceramic square rod formed with a laminate of a heater substrate on which a heater-patterned layer consisting of a heater element and leads is formed and a covering substrate covering the heater-patterned layer. Metallic terminals are connected electrically to the leads of the heater-patterned layer, respectively, and mounted on surfaces of the ceramic square rod opposed to each other in a direction of lamination of the heater substrate and the covering substrate, respectively. At least one outer lead is joined to one of the metallic terminals through a bonding layer.

16 Claims, 14 Drawing Sheets

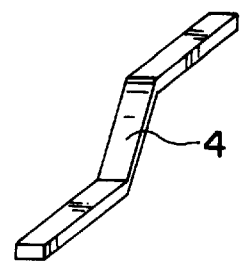
FIG. 8(a)
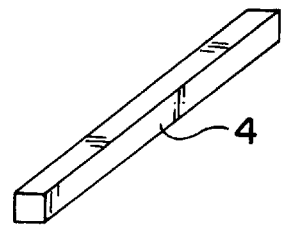
FIG. 8(b)
FIG. 9
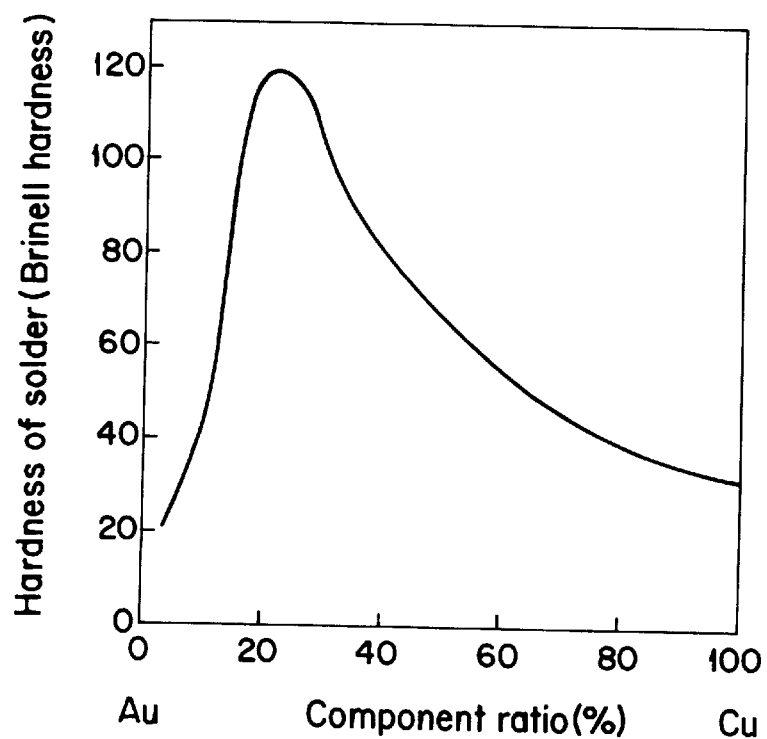

GAS SENSOR WITH CERAMIC HEATER

BACKGROUND OF THE INVENTION

1. Technical Field of the Invention

The present invention relates generally to a gas serLsor which may be employed in an air-fuel ratio control system for automotive vehicles for measuring the concentration of gas such $O_2$, NOx, or CO, and more particularly to an improved structure of a ceramic heater used in gas sensors and a manufacturing method thereof.

2. Background Art

FIGS. 1(a) and 1(b) show one example of conventional ceramic heaters which is built in an oxygen sensor for use in air-fuel ratio control of automotive internal combustion engines. The ceramic heater 9 serves to heat a sensor element up to an elevated temperature to minimize a variation in measured value.

The ceramic heater 9 consists of a ceramic square rod 10 made of a laminate of heater substrates and a covering substrate and metallic terminals 3 mounted on side surfaces 15 of the rod 10. The metallic terminals 3 connect electrically with leads of a heater-patterned layer in the rod 10 and joined to outer leads 4 through solders 5, respectively.

In manufacturing the ceramic heater 9, green sheets 101 and 102, as shown in FIG. 2(a), whose main component is alumina are first prepared. Next, a conductive paste is applied to the surface of each of the green sheets 101 to form a heater-patterned layer 2 consisting of pairs of a heater element 21 and a lead 22. The two green sheets 101 and the covering green sheet 102 are laid to overlap each other to form a three-layer laminate. The three-layer laminate is cut into several pieces as shown in FIG. 2(b). The metallic terminals 3 are formed on the side surfaces 15 of each piece which communicate electrically with the leads 22 to make an intermediate. Subsequently, the intermediate is baked, after which the outer leads 4 is, as shown in FIG. 2(c), welded to the metallic terminals 3 through the solder 5. Finally, welded portions of the outer leads 4 are, as indicated at numeral 6 in FIG. 1(b), plated with Ni to make the ceramic heater 9.

The above ceramic heater 9 and the manufacturing method thereof, however, have the following drawbacks.

The metallic terminals 3 are, as described above, mounted on the side surfaces 15 of the ceramic heater 9. It is, thus, only possible to attach the metallic terminals 3 to the square rod 10 after the three-layer laminate is cut as shown in FIG. 2(b). In other words, a large number of terminal attachment processes are required in mass-production of ceramic heaters.

In addition, the performance of the ceramic heater 9 is usually inspected after the outer leads 4 are mounted thereon. A large number of individual inspections are also required in the mass-production of ceramic heaters, thus resulting in an increase in manufacturing cost.

Another problem is also encountered in that the ceramic heater 9 is lower in durability than a round rod heater 91 as shown in FIG. 3(a). The results of heat cycle tests show that portions of the ceramic heater 9 welded to the outer leads 4 and the metallic terminals 3 tend to be cracked as compared with the round rod heater 91. This is because the angle β which each of the metallic terminals 3 of the ceramic heater 9, as shown in FIG. 4, makes with the outer surface of the solder 5 is greater than the angle α which each of the metallic terminals 3 of the round rod heater 91, as shown in FIG. 3(b), makes with the outer surface of the solder 5. The difference between the angles α and β depends upon the geometry of the heaters 9 and 91 and thus is difficult to eliminate. The use of solder which is soft enough to absorb internal stress ensures substantially the same durability of the portions of the rod 10 welded to the leads 4 as that of the round rod heater 91, however, square rod heaters exhibiting higher durability even in use of harder solder is sought.

SUMMARY OF THE INVENTION

It is therefore a principal object of the present invention to avoid the disadvantages of the prior art.

It is another object of the present invention to provide an easy-to-manufacture ceramic heater used in gas sensors which has a high durability and a manufacturing method thereof.

According to one aspect of the invention, there is provided a ceramic heater which may be employed in an air-fuel ratio control system for automotive vehicles for measuring the concentration of gas such $O_2$, NOx, or CO. The ceramic heater comprises: (a) a ceramic square rod formed with a laminate of a heater substrate on which a heater-patterned layer consisting of a heater element and leads connected to the heater element is formed and a covering substrate covering the heater-patterned layer of the heater substrate; (b) metallic terminals connected electrically to the leads of the heater-patterned layer of the heater substrate, respectively, the metallic terminals being mounted on surfaces of the ceramic square rod opposed to each other in a direction of lamination of the heater substrate and the covering substrate, respectively; and (c) at least one outer lead joined to one of the metallic terminals through a bonding layer.

In the preferred mode of the invention, a second outer lead is further joined to the other metallic terminal through a bonding layer.

The metallic terminals are electrically connected to the leads through holes formed in at least one of the covering substrate and the heater substrate.

Each of the metallic terminals is mounted on an area inside edges of the surface of the ceramic square rod.

The bonding layer occupies an area of a surface of the metallic terminal inside edges of the metallic terminal.

The one of the metallic terminals contains 70 Wt % of W or more. The bonding layer contains 40 to 98 Wt % of Cu and 2 to 20 Wt % of Ni.

The bonding layer may contain 60 Wt % of Au or less.

An Ni-plated layer may be formed on the one of the metallic terminals, having a thickness of 3 μm or less. The outer lead is joined to the Ni-plated layer through the bonding layer.

According to the second aspect of the invention, there is provided a ceramic heater. The ceramic heater comprises: (a) a ceramic square rod formed with a laminate of heater substrates each having formed thereon a heater-patterned layer comprising of a heater element and first and second leads connected to the heater element and a covering substrate interposed between the heater substrates; (b) first and second metallic terminals connected electrically to the first and second leads of the heater-patterned layers of the heater substrates, respectively, the metallic terminals being mounted on surfaces of the ceramic square rod opposed to each other in a direction of lamination of the heater substrates and the covering substrate; and (c) outer leads joined to the first and second metallic terminals through bonding layers, respectively.

In the preferred mode of the invention, the first metallic terminal is connected to the first leads of the heater substrates through conductive material-coated holes formed in the covering substrate and one of the heater substrates. The second metallic terminal is connected to the second leads of the heater substrates through conductive material-coated holes formed in the covering substrate and the other heater substrate.

Each of the bonding layers occupies an area of a surface of one of the metallic terminals inside edges of the metallic terminal.

Each of the metallic terminals contains 70 Wt % of W or more. Each of the bonding layers contains 40 to 98 Wt % of Cu and 2 to 20 Wt % of Ni.

Each of the bonding layers contains 60 Wt % of Au or less.

An Ni-plated layer formed on each of the metallic terminals, having a thickness of 3 μm or less. The outer leads are joined to the Ni-plated layers through the bonding layers.

According to the third aspect of the invention, there is provided a method of manufacturing ceramic heaters which comprises the steps of: (a) preparing a first green sheet; (b) preparing a second green sheet; (c) printing a first surface of the second green sheet an array of heater-patterned layers each consisting of a heater element and leads connected to the heater element; (d) printing a second surface of the second green sheet opposite the first surface with an array of metallic terminals; (e) attaching the first green sheet to the second green sheet so as to cover the first surface of the second green sheet to form a laminate; (f) baking the laminate to form a ceramic board; (g) joining outer leads to the metallic terminals through bonding layers, respectively; and (h) cutting the ceramic board into a plurality of square rods constituting units of the ceramic heaters.

In the preferred mode of the invention, a step is fur-her provided which forms through holes in the first green sheet for electrical connections of the leads of the heater-patterned layers and the metallic terminals.

A step is further provided which forms grooves in a surface of the ceramic board between adjacent two of the units of the ceramic heaters to be cut by the cutting step.

According to the fourth aspect of the invention, there is provided a method of manufacturing ceramic heaters which comprises the steps of: (a) preparing a first green sheet; (b) preparing second green sheets; (c) printing a first surface of each of the second green sheets an array of heater-patterned layers each consisting of a heater element and leads connected to the heater element; (d) printing a second surface of each of the second green sheets opposite the first surface with an array of metallic terminals; (e) interposing the first green sheet between the second green sheets so as to cover the first surfaces of the second green sheets to form a laminate; (f) baking the laminate to form a ceramic board; (g) joining outer leads to the metallic terminals formed on at least one of the second green sheets through bonding layers, respectively; and (h) cutting the ceramic board into a plurality of square rods constituting units of the ceramic heaters.

According to the fifth aspect of the invention, there is provided a gas sensor which comprises: (a) a gas sensing element having a gas-exposed portion, the gas sensing element having formed therein a chamber; (b) a ceramic heater disposed within the chamber of the gas sensing element to heat the gas sensing element; (c) a first cylindrical holder fitted in the chamber of the gas sensing element, the first holder including a heater holding portion for holding the ceramic heater and a sensor contact in contact with an inner wall of the gas sensing element, the sensor contact having a sensor signal output terminal; (d) a second cylindrical holder mounted on an outer wall of the gas sensing element, having a sensor signal output terminal; and (e) a slit formed in the first holder to define a C-shaped cross section, the slit being located 90°±20° apart from the sensor signal output terminal of the first cylindrical holder. The ceramic heater includes, (a) a ceramic square rod formed with a laminate of a heater substrate on which a heater-patterned layer consisting of a heater element and leads connected to the heater element is formed and a covering substrate covering the heater-patterned layer of the heater substrate, (b) metallic terminals connected electrically to the leads of the heater-patterned layer of the heater substrate, respectively, the metallic terminals being mounted on surfaces of the ceramic square rod opposed to each other in a direction of lamination of the heater substrate and the covering substrate, respectively, and (c) at least one outer lead joined to one of the metallic terminals through a bonding layer.

In the preferred mode of the invention, the sensor signal output terminal of the first cylindrical holder is located 180° apart from the sensor signal output terminal of the second cylindrical holder.

The slit is located 90° apart from the sensor signal output terminal of the first cylindrical holder.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to l-he specific embodiments but are for the purpose of explanation and understanding only.

In the drawings:

FIG. 1(*b*) is a cross sectional view taken along the line A—A in FIG. 1(*a*);

FIG. 3(*b*) is a cross sectional view taken along the line B—B in FIG. 3(*a*);

FIG. 5(*b*) is a sectional view taken along the line C—C in FIG. 5(*a*);

FIGS. 8(*a*) and 8(*b*) show modifications of an outer lead connected to a ceramic heater;

FIG. 9 is a graph which shows the relation between the hardness of solder and a component ratio of Au to Cu of the solder;

DESCRIPTION OF THE PREFERRED EMBODIMENTS

Figure 5A:
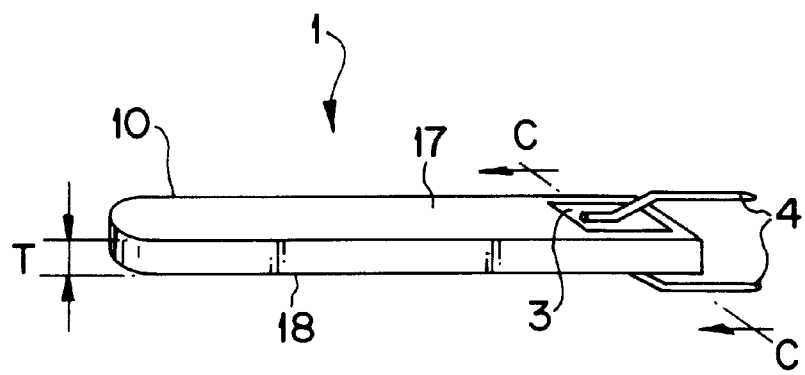
FIG. 5(*a*) is a perspective view which shows a ceramic heater according to the invention.
Figure 5B:
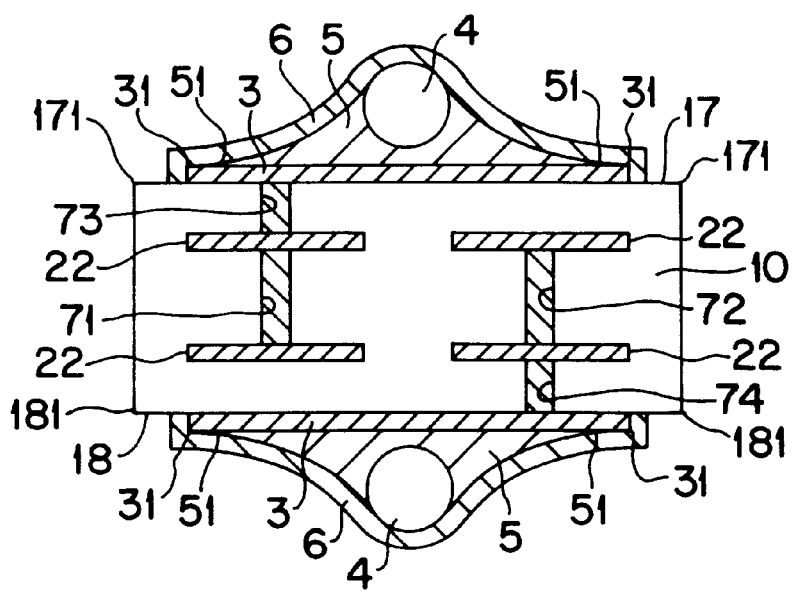

Referring now to the drawings, wherein like numbers refer to like parts in several views, particularly to FIG. 5(a) and 5(b), there is shown a ceramic heater 1 of an oxygen sensor according to the invention which is employed in automotive air-fuel ratio control systems to measure an oxygen content in exhaust gasses of an internal combustion engine. Note that the present invention is not limited to an oxygen sensor and may alternatively be used with a variety of gas sensors such as HC, CO, and NOx sensors.

Figure 6:
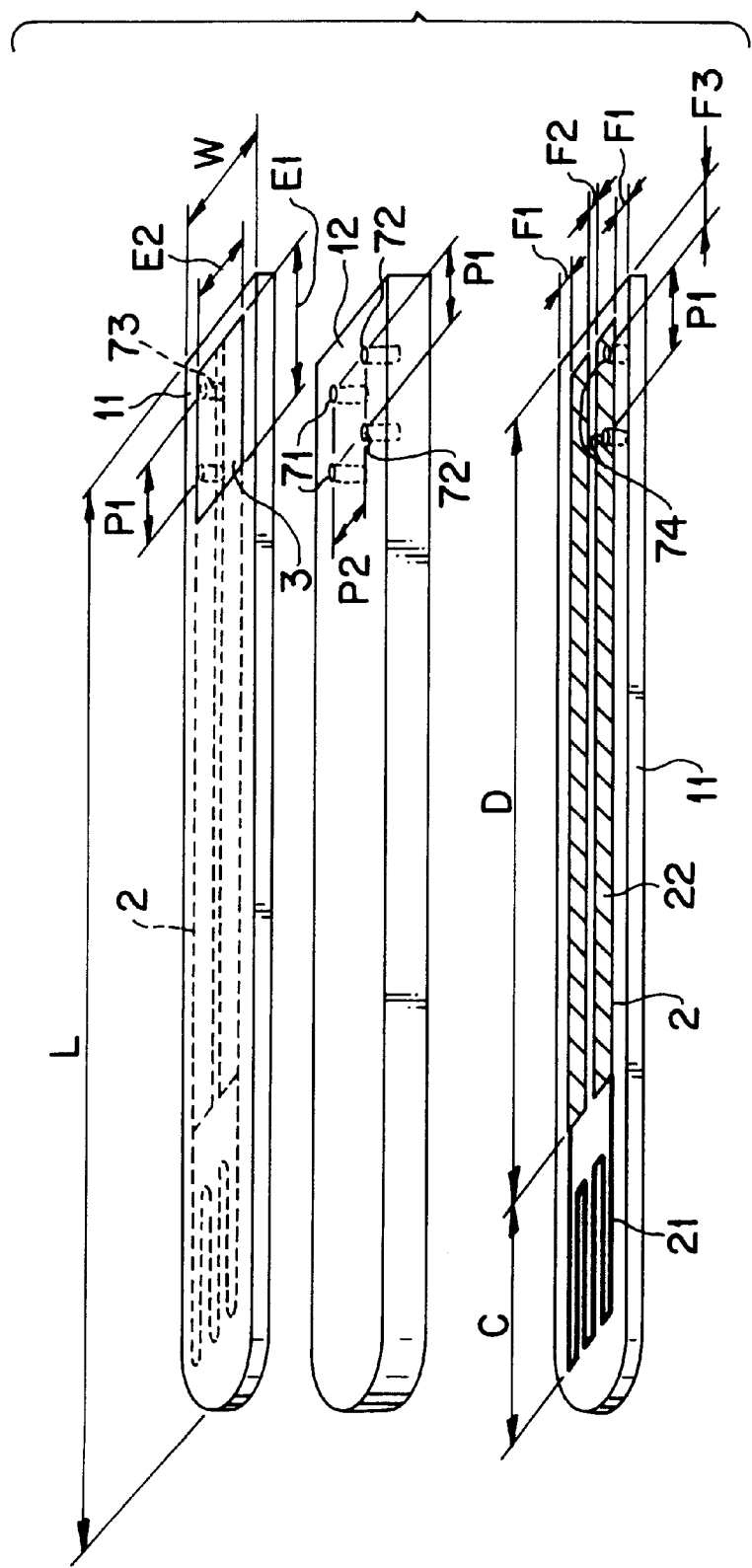
FIG. 6 is an exploded view which shows the ceramic heater in FIG. 5(*a*)

The ceramic heater 1 includes a ceramic square rod 10 which is, as clearly shown in FIG. 6, made of a laminate of two h(eater substrates 11 and a covering substrate 12. Each of the heater substrate 11 has formed thereon a heater-patterned layer 2 consisting of a heater element 21 and leads 22 connected to the heater element 21. The covering substrate 12 is interposed between the heater substrates 11 to cover the heater-patterned layers 2.

The ceramic heater 1 also includes a pair of metallic terminals 3 which are attached to upper and lower surfaces 17 and. 18, as viewed in FIGS. 5(a) and 5(b), of the heater substrates 11 and which are electrically connected to the leads 22. Outer leads 4 are welded to the terminals 3 through bonding layers 5, respectively.

The covering substrate 12 and the heater substrates 11, as clearly shown in FIGS. 5(b) and 6, have conductive material-coated through holes 71, 72, 73, and 74, respectively, to establish electrical communication between the heater-patterned layers 2 of the heater substrates 11 and the metallic terminals 3.

The metallic terminals 3 are, as clearly shown in FIG. 5(b), disposed on flat portions of the surfaces 17 and 18 of the heater substrates 11 so that side ends 31 thereof may be located inside side edges 171 and 181 of the heater substrates 11, respectively.

The bonding layers 5 are formed with solder made of, for example, Cu/Si, Cu/Au, or Cu/Ni material and, as can be seen in FIG. 5(b), formed on flat surfaces of the terminals 3 so that side edges 51 thereof may be located inside the side ends 31 of the terminals 3.

The ceramic square rod 10 has, as shown in FIG. 6, an overall length L of 54 mm, an overall width W of 2.9 mm, and a thickness T of 1.6 mm (see FIG. 5(a)). The length C of the heater element 21 of each of the heater-patterned layers 2 is 9 mm. The length D of each of the leads 22 is 42 mm.

The leads 22 formed on each of the heater substrates 11 extend in parallel at an interval F2 of 0.228 mm away from each other. Each of the leads 22 is disposed at an interval F1 of 0.25 mm away from the side of the heater substrate 11 and at an interval F3 of 1 mm away from a rear end of the heater substrate 11.

The through holes 71 to 74 are arrayed with a pitch P1 of 3.6 mm in a lengthwise direction of the heater substrate 11 and a pitch P2 of 1.4 mm in a widthwise direction of the heater substrate 11 and have a diameter of 3 mm. The metallic terminals 3 each have a length E1 of 5.5 mm and a width E2 of 2.3 mm.

A sequence of manufacturing processes of the ceramic heater 1 will be discussed below with reference to FIGS. 7(a), 7(b), and 7(c).

A powdered raw material containing about 92 Wt % of $Al_2O_3$ and a total of about 8 Wt % of $SiO_2$, CaO, and MgO is first prepared to make slurry.

Next, a green sheet is formed with the slurry using the doctor blade and then punched by a punch press to form green sheets 101 measuring 120 mm×120 mm for making the heater substrates 11 and a green sheet 102 measuring 120 mm×120 mm for making the covering substrate 12. The through holes 71 to 74 are formed in the green sheets 101 and 102.

The making of the green sheets 101 and 102 may alternatively be achieved with the extrusion molding.

Figure 7A:
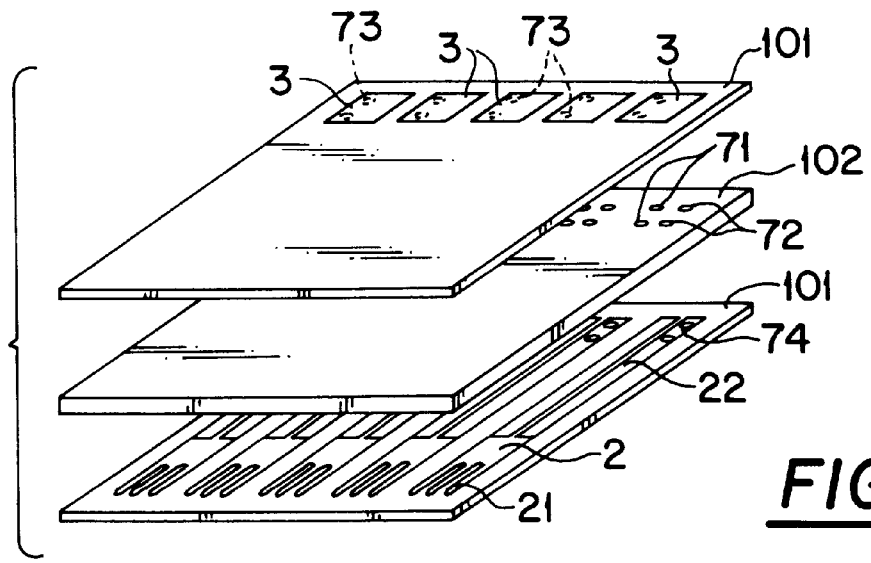
FIGS. 7(*a*), 7(*b*), and 7(*c*) are perspective views which show a sequence of manufacturing processes of a ceramic heater.

A conductive paste whose main constituent is metal such as W or Mo is prepared and coated on surfaces of the green sheets 101 to form heater-patterned layers 2, as shown in FIG. 7(a), and inner walls of the through holes 71 to 74 using printing techniques. The heater-patterned layers extend parallel to each other.

On a surface of each of the green sheets 101 opposite to the heater-patterned layers 2, a conductive paste is coated to form the metallic terminals 3 in line using printing techniques. The conductive paste is made of a main constituent of metal containing 70 Wt % or more of W and a remaining content of Mo, but may be identical with that used in forming the heater-patterned layers 2.

The two green sheets 101 are arranged so that the heater-patterned layers 2 may face each other. Subsequently, the green sheet 102 is interposed between the green sheets 101 to form a three-layer laminate. The three-layer laminate is baked at 1400 to 1600° C. in a reducing atmosphere of $N_2$ and $H_2$ gasses to make an intermediate.

Figure 7B:
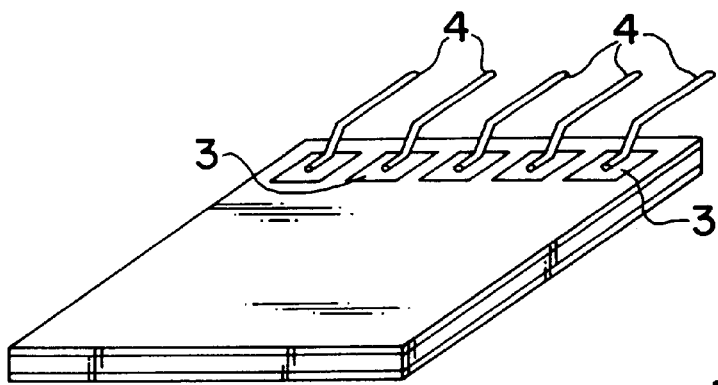

The outer leads 4 are, as shown in FIG. 7(b), soldered to the metallic terminals 3, respectively. The soldering is achieved by placing solder and the outer leads 4 on the metallic terminals 3 and heating them at 1000 to 1200° C. to form the bonding layers 5.

Each of the outer leads 4 may be made either of a round bar, as shown in FIG. 7(b), or of a square bar, as shown in FIGS. 8(b) and 8(b).

The overall surface of each of the bonding layers 5 is, as clearly shown in FIG. 5(b), covered with an Ni-plated layer 6.

Figure 7C:
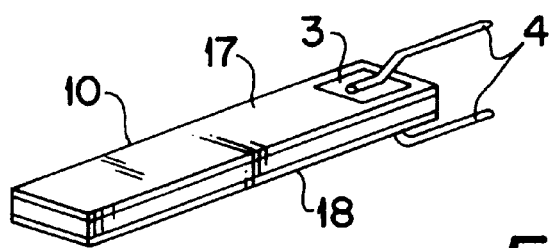

The intermediate is, as shown in FIG. 7(c), cut into several pieces, i.e., units of the ceramic heaters 1.

Finally, an end of each of the ceramic heaters 1 opposite to the outer leads 4 is rounded using a grinding machine.

Note that after the three-layer laminate is braked, the intermediate is tested for heater performance.

Each of the bonding layers 5 may contain 40 to 98 Wt % of Cu and 2 to 20 Wt % of Ni. The metallic terminals 3, as described above, contains W, thus resulting in improved wettability between the bonding layers 5 and the metallic terminals 3, which eliminates the need for the metallic terminals 3 to be plated with Ni in conventional manufacturing processes.

When the content of Cu in the bonding layers 5 is small, less than 40 Wt % and when the leads 4 do not contain Ni, it will cause no Ni to be diffused from the leads 4 to the bonding layers 53, so that the content of Ni in the bonding layers 5 will be smaller than that when the content of Cu is more than 40 Wt %, which results in lowered wettability of the bonding layers 5 to the metallic terminals 3 and a decrease in strength of joints of the bonding layers 5 and the metallic terminals 3.

When the content of Cu in the bonding layers 5 is greater than 98 Wt %, the content of Ni in the bonding layers 5 will be smaller than that in the metallic terminals 3, thereby causing the wettability of the bonding layers 5 to the metallic terminals 3 to be lowered, which results in a decrease in strength of the joints of the bonding layers 5 and the metallic terminals 3.

When the content of Ni in the bonding layers 5 is less than 2 Wt %, it will cause the wettability of the bonding layers 5 to the metallic terminals 3 to be lowered, resulting in a decrease in strength of the joints of the bonding layers 5 and the metallic terminals 3. Alternatively, when the content of Ni in the bonding layers 5 greater than 20 Wt %, it will cause a W-Ni intermetallic compound to be precipitated during manufacture, resulting in a decrease in strength of joints of the bonding layers 5 and the metallic terminals 3.

The metallic terminals 3 contain, as described above, 70 Wt % of W or more (including 100 Wt % of W) and thus have good conformability to a ceramic particularly containing alumina (i.e., the square rod 10 of the ceramic heater 1) and good heat resistance. When the content of W is less than 70 Wt %, it may result in decreases in strength of a joint of the metallic terminals 3 and the square rod 10 and heat resistance.

The bonding layers 5 may contain 60 Wt % of Au or less for avoiding precipitation of a W—Ni intermetallic compound to increase the strength to join the leads 4 to the metallic terminals 3. When the content of Au in the bonding layers 5 is more than 50 Wt %, the content of Cu will be decreased. Thus, when the leads 4 do not contain Ni, it will cause no Ni to be diffused from the loads 4 to the bonding layers 5, so that the content of Ni in the bonding layers 5 will be smaller than that when the content of Au is less than 60 Wt %, which results in lowered wettability of the bonding layers 5 to the metallic terminals 3 and a decrease in strength of joints of the bonding layers 5 to the metallic terminals 3. Specifically, when the content of Au is, as shown in FIG. 9, 60 to 90 Wt %, the hardness of the solder forming the bonding layers 5 becomes too high, thus resulting in a decrease in durability against cyclic changes in ambient temperature. When the content of Au is greater than 90 Wt %, the hardness of the solder is lower, but manufacturing costs will increase.

A major surface of each of the metallic terminals 3 to which the leads 4 are to be joined through the bonding layer 5 may be plated with Ni. The thickness of the Ni-plated layer is 3 or less µm. The formation of the Ni-plated layer improves the wettability of the bonding layer 5, thereby decreasing the welded angle which the outer surface of each side end of the bonding layer 5 makes with the metallic terminal 3, resulting in a decrease in thermal stress contributing to cracks. When the thickness of the Ni-plated layer is more than 3 µm, a metallic alloy will be produced between the Ni-plated layer and the metallic terminal 3 which decreases the strength to join the bonding layer 5 and the metallic terminal 3.

The laminate produced in the process shown in FIG. 7(a) may consist only of the single green sheet 101 and the green sheet 102. In this case, the metallic terminals 3 are also formed on a surface of the green sheet 102 opposite to a surface covering the heater-patterned layers 2 of the green sheet 101.

As can be seen from the above discussion, the metallic terminals 3 and the outer leads 4 are disposed on the surfaces 17 and 18 of the square rod 10 opposed in a direction of lamination of the substrates 11 and 12, thereby allowing the joining process wherein the outer leads 4 are joined to the metallic terminals 3, respectively, to be performed before the intermediate is cut into units of the ceramic heaters 1 in the course of manufacture. This will result in great rationalization of the manufacturing processes.

In addition, the performance test may be, as described above, performed before the intermediate is cut into unit of the ceramic heaters 1, thus resulting in rationalization of procedure of the test.

The metallic terminals 3 and the bonding layers 5 are, as described above, arranged on the surfaces 17 and 18 cf the square rod 10 out of alignment of side ends with each other, thus avoiding concentration of stress on the side edges 171, 181, 31, and 51, which will result in improved durability of the ceramic heater 1.

One of the metallic terminals 3 of the ceramic heater 1 may be connected directly to a connector leading to, for example, a ground terminal without use of the outer lead 4. In this case, the single outer lead 4 may be joined to either of the metallic terminals 3.

Figure 10:
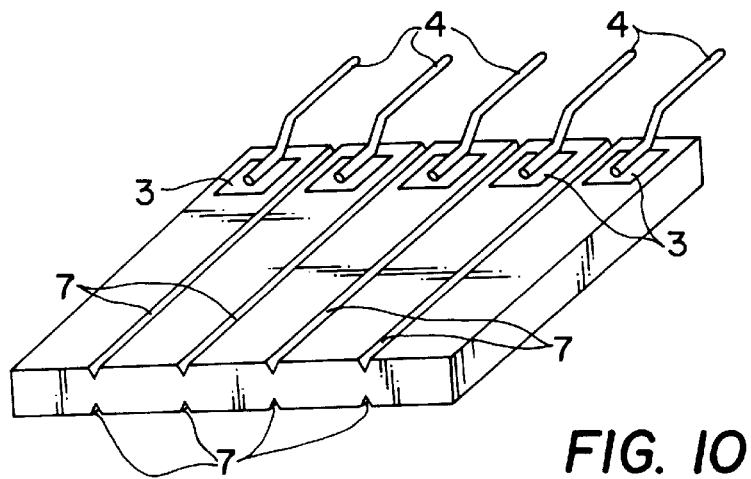
FIG. 10 shows the second embodiment of the manufacturing processes of the ceramic heater 1.

FIG. 10 shows the second embodiment of the manufacturing processes of the ceramic heater 1.

Before the three-layer laminate of the green sheets 101 and 102 is braked, cutting notches or grooves 7 are machined in upper and lower surfaces of the three-layer laminate which extend parallel between adjacent two of the metallic terminals 3 for facilitating ease of cutting the three-layer laminate into units of the ceramic heaters 1 after being baked.

The formation of the cutting grooves 7 is achieved by grooving the upper and lower surfaces of the three-layer laminate to a depth less than half a thickness of the laminate using a cutting machine.

Other manufacturing processes are identical with those of the first embodiment, and explanation thereof in detail will be omitted here.

Figure 1A:
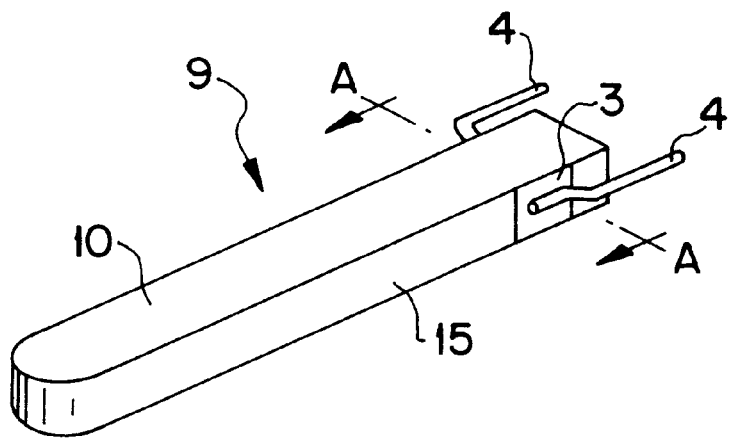
FIG. 1(*a*) is a perspective view which shows a conventional ceramic heater.
Figure 1B:
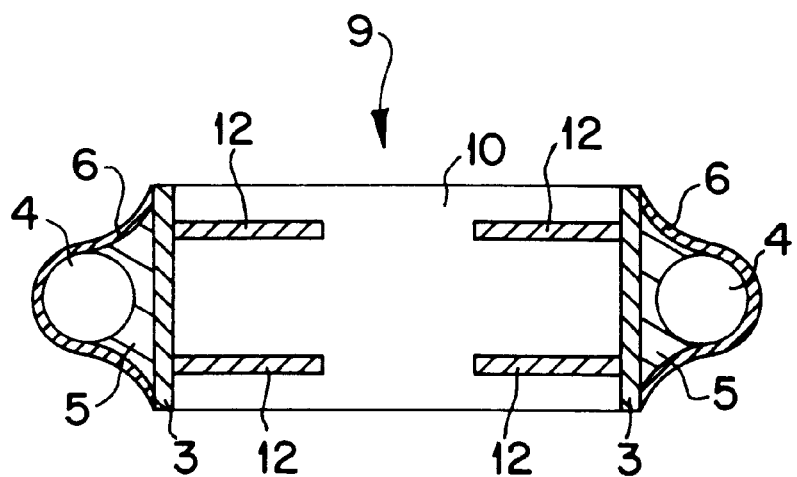
Figure 2A:
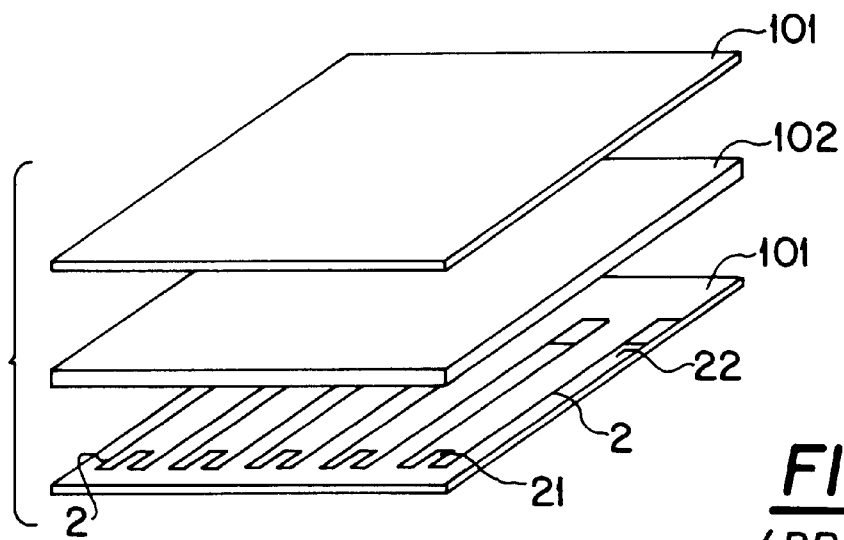
FIGS. 2(*a*), 2(*b*), and 2(*c*) are perspective views which show a sequence of manufacturing processes of a conventional ceramic heater.
Figure 2B:
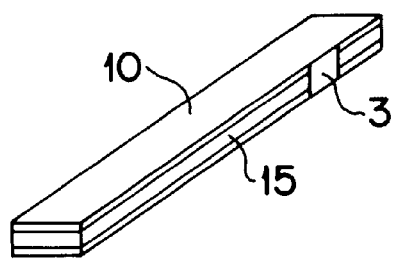
Figure 2C:
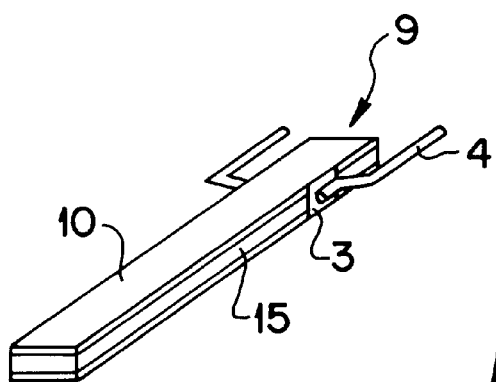
Figure 3A:
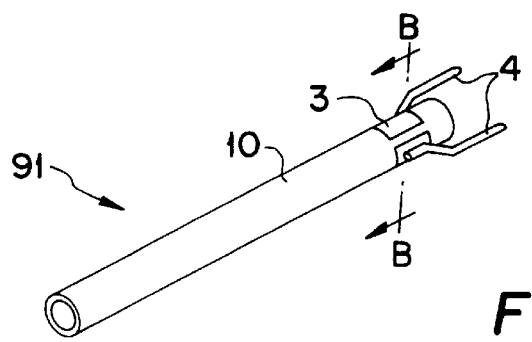
FIG. 3(*a*) is a perspective view which shows a conventional ceramic heater made of a round bar.
Figure 3B:
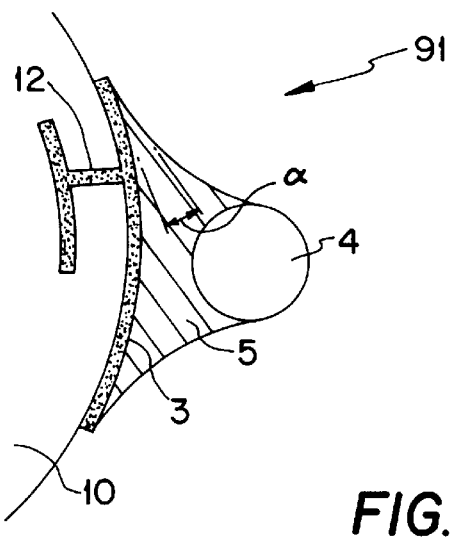
Figure 4:
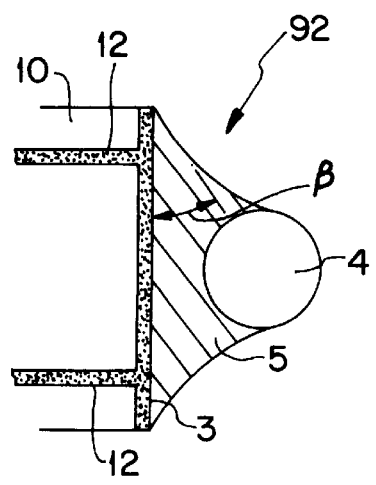
FIG. 4 is a sectional view which shows a welded angle of an outer surface of an end of a bonding layer with a metallic terminal.
Figure 11A:
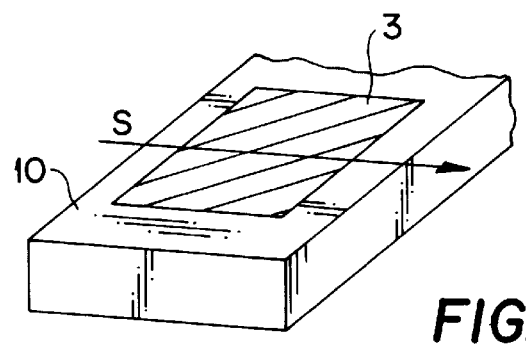
FIGS. 11(a) and 11(b) show manners to measure the surface roughness of a metallic terminal of the invention and a conventional metallic terminal.
Figure 11B:
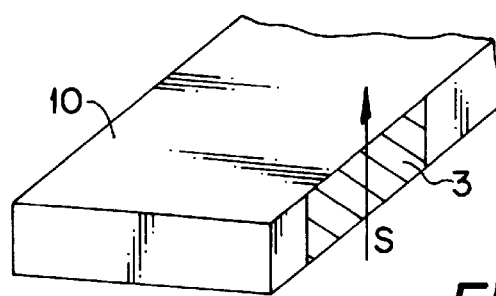

Ten samples of the ceramic heater 1 made in the manufacturing processes of the first embodiment were tested for the surface roughness of the metallic terminals 3 which may be thought of as one of factors of improvement of durability. The measurement of the surface roughness was accomplished, as shown in FIG. 11(a), by scanning the surface of the metallic terminal 3 of each sample over 0.8 mm in a direction, as indicated by S in FIG. 11(a). For comparison, the same tests were performed, as shown in FIG. 11(b), for ten conventional ceramic heaters identical with the one shown in FIGS. 1(a) and 1(b). The results of the tests are shown in table 1 below.

TABLE 1

| Sample No. | Prior art ($\mu$m) | Invention ($\mu$m) |
| --- | --- | --- |
| 1 | 3.642 | 1.481 |
| 2 | 3.932 | 1.098 |
| 3 | 2.47 | 1.018 |
| 4 | 3.782 | 0.978 |
| 5 | 3.146 | 1.294 |
| 6 | 2.858 | 1.893 |
| 7 | 3.431 | 1.149 |
| 8 | 3.278 | 1.19 |
| 9 | 2.685 | 1.435 |
| 10 | 2.891 | 1.215 |
| Average | 3.212 | 1.275 |

The table 1 shows that the surface roughness (Rz) of the metallic terminals 3 of the ceramic heater 1 is greatly improved as compared with the conventional ceramic heaters. The improvement of the surface roughness of the metallic terminals will facilitate flow of solder on the surfaces of the metallic terminals 3 when the outer leads 4 are joined to the metallic terminals 3, thereby increasing an area of the bonding layers 5, which results in improvement of initial strength to join the outer leads 4 to the metallic terminals 3 and a decrease in thermal stress acting on the joints produced by cyclic temperature changes, thus improving the durability of the ceramic heater 1.

Figure 12:
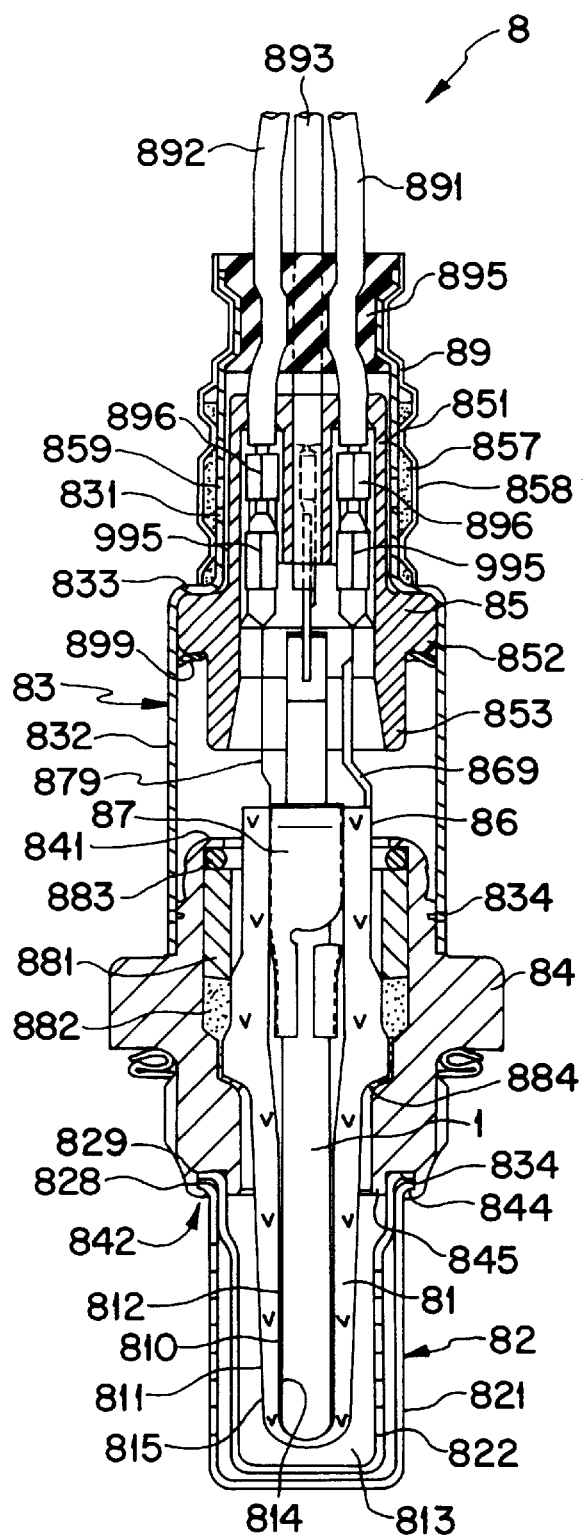
FIG. 12 is a vertical sectional view which shows an oxygen sensor in which the ceramic heater shown in FIGS. 5(a) and 5(b) is built.

FIG. 12 shows an oxygen sensor 8 in which the ceramic heater 1 is built.

The oxygen sensor 8 is used in an automotive internal combustion engine control system and includes a gas sensing element 81 with a gas-exposed portion 811 exposed to the gas to be measured.

The gas sensing element 81 is of a cup-shape having formed therein an inner chamber 810. Within the inner chamber 180, the ceramic heater 1 is disposed for heating the gas sensing element 81.

On outer and inner surfaces of the gas sensing element 81, minus and plus holders 86 and 87 are installed which have sensor signal output terminals 869 and 879, respectively. The pulse holder 87 includes, as shown in FIGS. 13(b) and 14(a) to 14(c), a heater holding portion 871 for holding the ceramic heater 1 and a sensor contact 873 for making contact with the inner surface of the gas sensing element 81. The sensor signal output terminal 879 extends from an end of the sensor contact 873. The heater holding portion 871 and the sensor contact 873 have formed therein slits 877 and 878 to define C-shape in section so that they may be elastically deformable to have spring properties. The slits 877 and 878 extend in a lengthwise direction of the pulse holder 87 and are shifted approximately 90° away from each other. The heater holding portion 871 and the sensor contact 873 are joined through a frusto-conical connector 872. The connector 872 has formed therein an L-shaped slit which connects the slits 877 and 878. The heater holding portion 871 and the sensor contact 873 are eccentric so that the ceramic heater 1 may be coaxial with the gas sensing element 81 when the plus holder 87 is fitted in the gas sensing element 81.

Figure 13A:
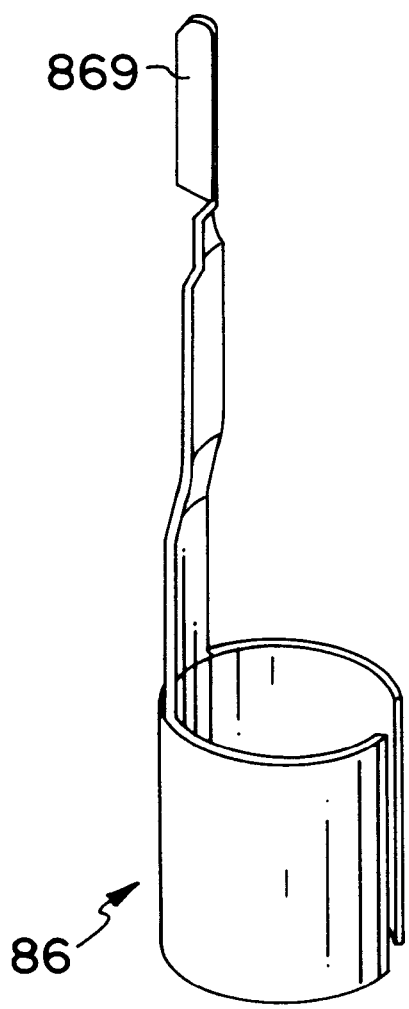
FIG. 13(a) is a perspective view which shows a minis holder for holding a gas sensing element.
Figure 13B:
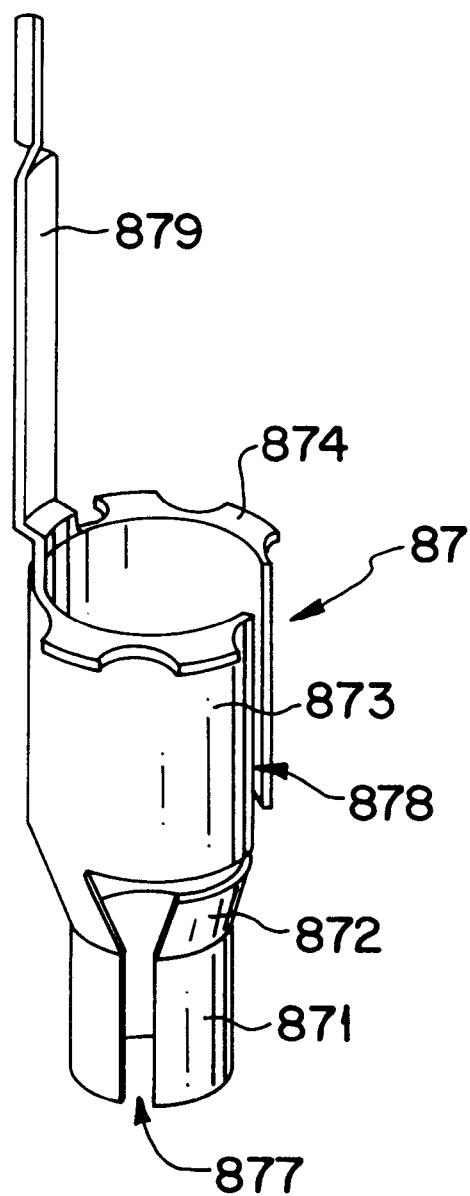
FIG. 13(b) is a perspective view which shows a plus holder for holding a ceramic heater.
Figure 14A:
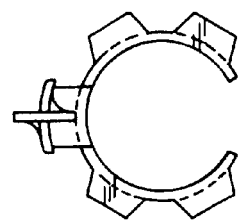
FIG. 14(a) is a plan view of a plus holder.
Figure 14B:
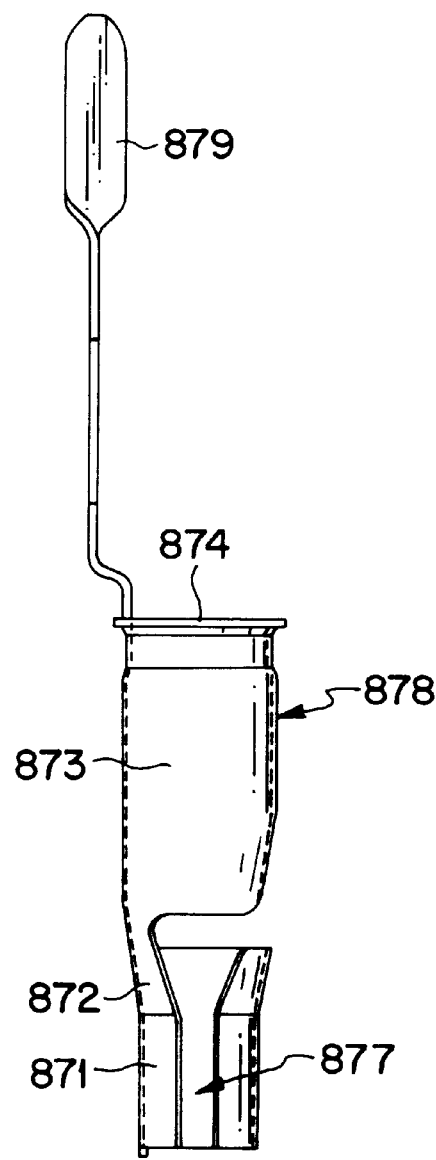
FIGS. 14(b) and 14(c) are side views of the plus holder in FIG. 14(a)
Figure 14C:
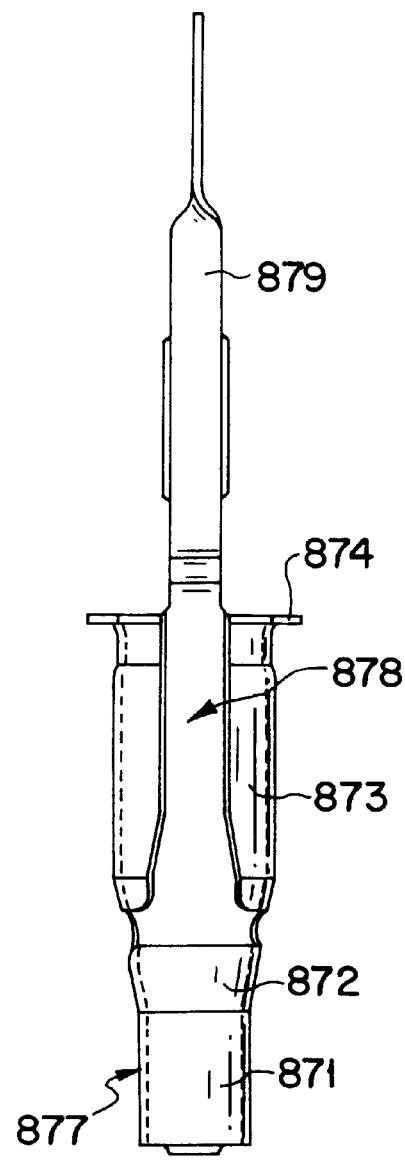

The slit 878 formed in the sensor contact 873 is, as can be seen in FIG. 13(b), diametrically opposed to the sensor signal output terminal 879 and thus is located at an angular interval of 90° away from the slit 877 formed in the heater holding portion 871.

The sensor contact 873 has formed on the end thereof a plurality of claws 874 which engage an upper end of the gas sensing element 81 for orientation to the gas sensing element B 1.

The sensor contact 873 has an outer diameter slightly greater than an inner diameter of the gas sensing element 81 so that the sensor contact 873 may be installed elastically within the gas sensing element 81 by a press fit. The heater holding portion 871 has an inner diameter slightly smaller than a maximum outer diameter of the ceramic heater 1 for establishing tight engagement with the ceramic heater 1 when fitted in the heater holding portion 871.

The minus holder 86, as clearly shown in FIG. 13(a), has formed therein a slit to have spring properties like the plus holder 87. In order to enhance the spring properties, the plus holder 87 and the minus holder 86 are both made of a heat resisting spring steel.

Figure 15A:
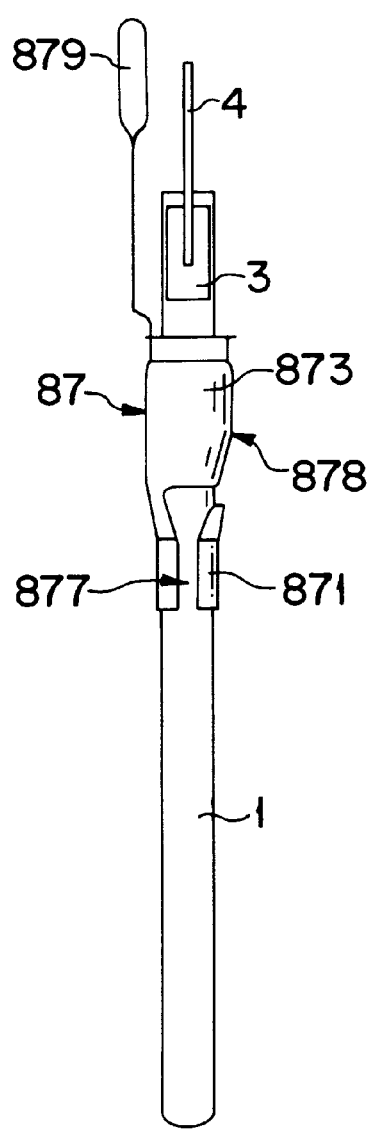
FIGS. 15(a) and 15(b) are side views of a plus holder in which a ceramic heater is fitted.
Figure 15B:
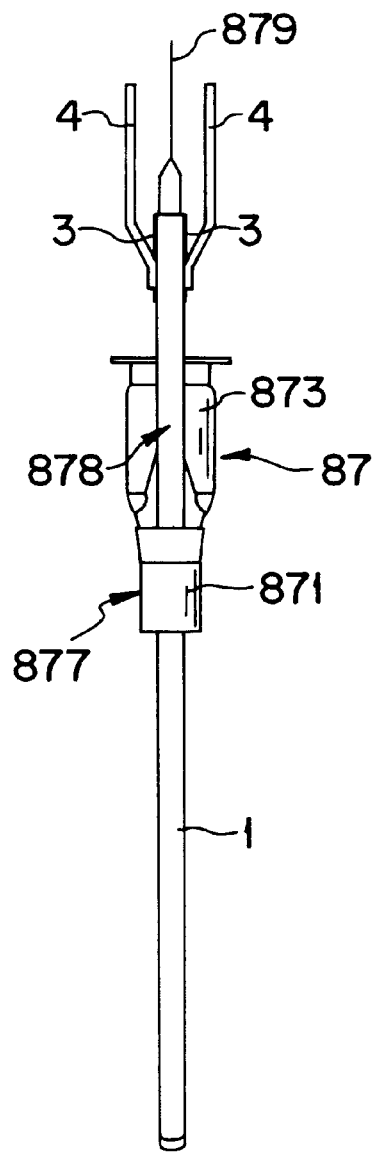
Figure 16:
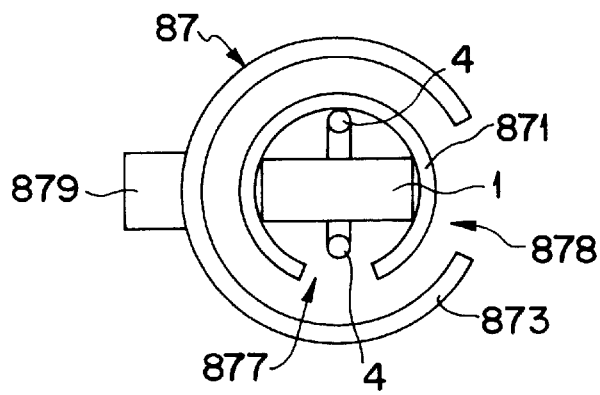
FIG. 16 is a plan view which shows a plus holder in which a ceramic heater is fitted.

FIGS. 15(a), 15(b), and 16 show the plus holder 87 in which the ceramic heater 1 is fitted. As clearly shown in FIG. 16, the ceramic heater 1 is disposed in the plus holder 87 with one of the surfaces on which the outer leads 4 are installed facing the slit 877 so that the outer leads 4 may be both located 90° apart from the sensor signal output terminal 879.

Figure 17:
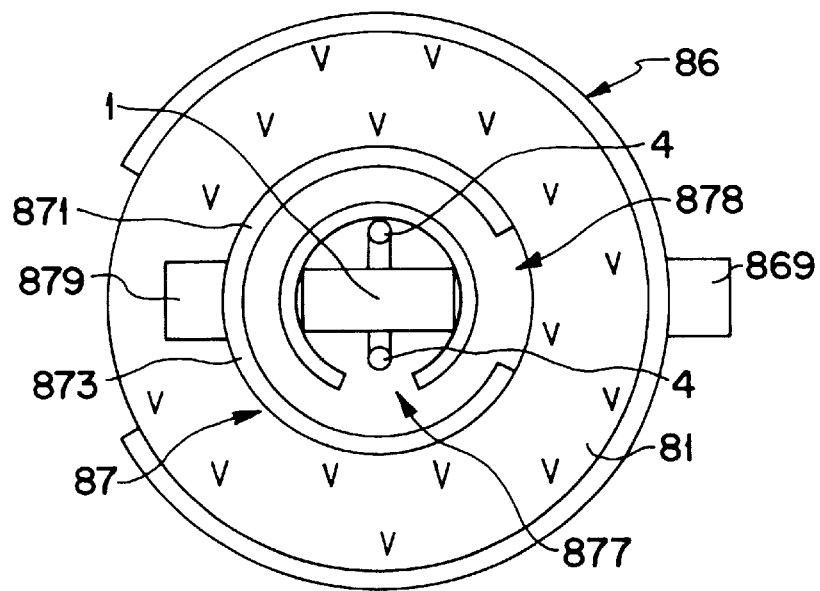
FIG. 17 is a plan view which shows a plus holder holding therein a ceramic holder fitted in a gas sensing element and a minus holder.

FIG. 17 shows the plus holder 87 holding therein the ceramic holder 1 fitted in the gas sensing element 81 and the minus holder 86 installed on the outer surface of the gas sensing element 81. The sensor signal output terminal 869 of the minus holder 86 is located approximately 1800 away from the sensor signal output terminal 879 of the plus holder 87. The sensor signal output terminals 869 and 879 are, therefore, arranged at angular intervals 90° away from the outer leads 4, respectively.

The gas sensing element 81 has, as shown in FIG. 12, a reference gas chamber 812 formed in the inner chamber 810 and defines a gas chamber 813 between itself and a protective cover assembly 82. An outer electrode 815 and an inner electrode 814 both made of platinum are installed on the gas-expose d portion 811 and the inner surface of the gas sensing element 81 in connection with the minus holder 815 and the plus holder 87, respectively.

The sensor signal output terminals 869 and 879 of the holders 86 and 87 and the leads 4 of the ceramic heater 1 are electrically connected to four leads 891 to 893, respectively, through connectors 995 and 896. The connectors 995 and 895 are disposed in an insulator 85 at regular intervals of 90° for avoiding interference with each other.

The gas sensing element 81 is installed in a sensor mount 84 which is used in mounting the oxygen sensor 8 in an exhaust pipe of an automotive engine. The protective cover assembly 82 is mounted on an end of the sensor mount 84 to cover the gas sensing element 81. A dust cover 83 is mounted on the sensor mount 84.

The sensor mount 84 has a cylindrical wall which extends upward from the flange thereof and in which an insulator 881, a talc 882, and a ring spacer 883 are disposed to retain the gas sensing element in the sensor mount 84. An end 841 of the cylindrical wall of the sensor mount 84 is crimped inward to elastically press the ring spacer 883 downward, as viewed in FIG. 12. A float packing 884 is interposed between an inner wall of the sensor mount 84 and an outer wall of the gas sensing element 81 to seal the gas chamber 813 hermetically.

The sensor mount 84 has formed in the end 842 thereof an annular groove 843 to form an outer skirt 844 and an inner skirt 845. The protective cover assembly 82 consists of an outer cover 821 and an inner cover 822 both made of a cup-shaped member. The outer and inner covers 821 and 822 have flanges 828 and 829 which are retained in the groove 843 of the sensor mount 84 by crimping the outer skirt 844 inward. The outer and inner covers 821 and 822 have formed in side walls thereof a plurality of holes through which a gas to be measured passes to enter the gas chamber 813.

The dust cover 83, as shown in FIG. 12, consists of a small-diameter cylinder 831, a large-diameter cylinder 832, and a shoulder portion 833 connecting the cylinders 831 and 832. The dust cover 83 is, as described above, welded at a circumferential portion 834 thereof to a boss of the sensor mount 84 and retains therein the insulator 85.

A cylindrical cover 839 is mounted on the periphery of the small-diameter cylinder 831 of the dust cover 83 by crimping. A water-repellent filter 857 is installed between the cylindrical cover 839 and the small-diameter cylinder 831. The cover 839 and the dust cover 83 have formed therein first air vents 858 and second air vents 859, respectively, which communicate with the reference gas chamber 812 formed in the gas sensing element 81 to fill the reference gas chamber 812 with air.

A heat-resisting rubber bush 895 is mounted in the end of the small-diameter cylinder 831 of the dust cover 83 to retain the leads 891 to 893 at angular intervals of 90°

The insulator 85 consists of a sleeve 851 in which the leads 891 to 893 are disposed and a flange 852 greater in diameter than the sleeve 851. The small-diameter cylinder 831 of the dust cover 83 has the inner diameter greater than the outer diameter of the sleeve 851 of the insulator 85 and smaller than the outer diameter of the flange 852. The large-diameter cylinder 832 of the dust cover 83 has the inner diameter greater than the outer diameter of the flange 852 of the insulator 85.

The insulator 85 is retained in the large-diameter cylinder 832 of the dust cover 83 in engagement of an upper end of the flange 852 with the shoulder portion 833 of the dust cover 83 by a stop ring 899 press-fitted in the large-diameter cylinder 832.

The gas sensing element 81 produces the electromotive force as a function of a difference in oxygen concentration between the air in the reference gas chamber 812 and the gas in the gas chamber 813 and outputs a signal indicative thereof through the leads 891 and 892. The operation of the oxygen sensor 8 is well known in the art, and explanation thereof in detail will be omitted here.

The operation and effects of this embodiment will be described below.

The four connectors 896 and 995 are disposed in an insulator 85 at regular intervals of 90° for avoiding interference with each other. The sensor signal output terminals 879 and 8,69 of the holders 86 and 87 and the leads 4 of the ceramic heater 1 are, therefore, located at regular intervals of 90° away from each other.

The sensor signal output terminal 879 installed on the sensor contact 873 of the plus holder 87 is, as described above, located approximately 90° away from the slit 877 formed in the heater holding portion 871, thereby allowing the ceramic heater 1 to be, as shown in FIGS. 16 and 17, fitted firmly in the heater holding portion 871 of the plus holder 87 so that the leads 4 of the ceramic heater 1 may be located at angular intervals of 90° away from the sensor signal output terminal 879.

Figure 18A:
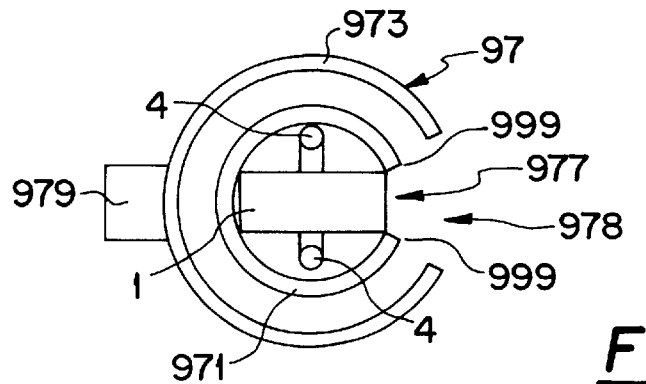
FIGS. 18(a) and 18(b) are plan views which a comparative example.
Figure 18B:
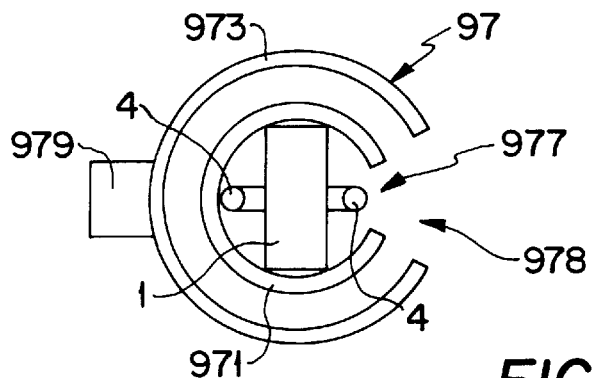

For comparison with this embodiment, a plus holder 97 used in conventional oxygen sensors is shown in FIGS. 18(a) and 18(b). The plus holder 97 has a slit 977 formed in a heater holding portion 971 at an angular interval of 180° away from a sensor signal output terminal 979. The slit 977 is located at the same angular position as that of a slit 978 formed in a sensor contact 973 of the plus holder 97. Arranging the leads 4 of the ceramic heater 1 90° apart from the sensor signal output terminal 979 requires, as shown in FIG. 18(a), retaining side walls of the ceramic heater 1 between vertical edges 999 and an opposite inner wall of the heater holding portion 971 defining the slit 977, thus resulting in instability of installation of the ceramic heater 1.

The stable installation of the ceramic heater 1 in the plus holder 97 requires, as shown in FIG. 18(b), retaining the side walls of the ceramic heater 1 between opposite portions of the inner wall of the plus holder 97 located 90° apart from the slit 977. In this case, the leads 4 are oriented in alignment with the sensor signal output terminal 979, so that they are twisted undesirably when connected to the connectors 896 and 995.

The structure of this embodiment allows, as described above, the leads 4 of the ceramic heater 1 to be located 90° apart from the sensor signal output terminal 879 without compromising the installation of the ceramic heater 1 in the plus holder 87.

The positional relation between the sensor signal output terminal 879 of the sensor contact 973 and the slit 877 of the heater holding portion of the plus holder 87 is not limited to 90°, but may be within an angular range of 90°±20°. This also achieves firm installation of the ceramic heater 1 in the plus holder 87 without interfering the connectors 896 and 995 with each other.

Figure 19:
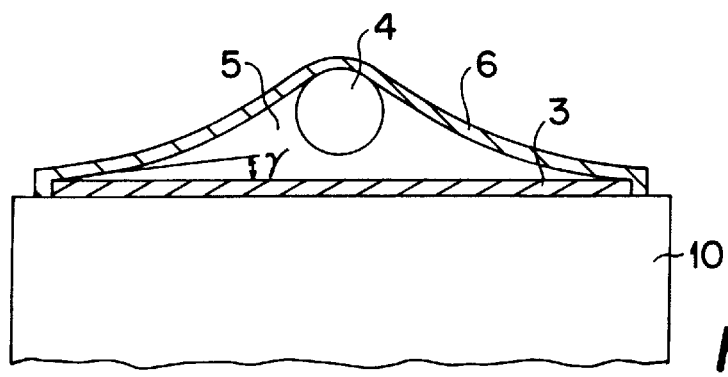
FIG. 19 is a sectional view which shows a welded angle of an outer surface of an end of a bonding layer with a metallic terminal.

The inventors of this application analyzed the relation between the durability of the ceramic heater 1 and a welded angle which the outer surface of each side end of the bonding layer 5 makes with the metallic plate 3. The analysis was made by preparing samples whose welded angles $\gamma$, as shown in FIG. 19, are 25° to 60° and performing a temperature cycle test a hundred times in which each sample was subjected to intense heat at 450° C. for four minutes and then left at room temperature for four minutes. After the hundred temperature cycle tests, each metallic terminals 3 was checked for cracks, and the strength of a joint of the bonding layer 5 and the metallic terminal 3 was measured. The measurement of the strength was performed in tensile tests. The results of the tests are shown in table 2 below.

TABLE 2

| Welded Angle $\gamma$ | Cracks | Joint Strength (kgf) | Evaluation |
| --- | --- | --- | --- |
| 60° | many | 1 or less | X |
| 50° | many | 1 or less | X |
| 40° | few | 3 | Δ |
| 30° | few | 4 | ○ |
| 20° | few | 4.5 | ○ | where ○ indicates excellent durability, Δ indicates allowable durability, and X indicates lack of durability.

The table 2 shows that the ceramic heater 1 has high durability when the welded angle $\gamma$ is 40° or less.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principles of the invention as set forth in the appended claims.

What is claimed is:

1. A ceramic heater comprising:

a ceramic square rod formed by a lamination of a heater substrate on which a heater-patterned layer comprising a heater element and leads connected to the heater element is formed and a covering substrate covering the heater-patterned layer of the heater substrate;

metallic terminals connected electrically to the leads of the heater-patterned layer of the heater substrate, respectively, said metallic terminals being mounted on surfaces of said ceramic square rod opposed to each other in a direction of lamination of the heater substrate and covering substrate, respectively; and at least one outer lead joined to one of said metallic terminals through a bonding layer made of solder.

2. A ceramic heater as set forth in claim 1, further comprising a second outer lead joined to the other metallic terminal through a bonding layer.

3. A ceramic heater as set forth in claim 1, wherein said metallic terminals are electrically connected to the leads through holes formed in at least one of the covering substrate and the heater substrate.

4. A ceramic heater as set forth in claim 1, wherein each of said metallic terminals is mounted on an area inside edges of the surfaces of said ceramic square rod.

5. A ceramic heater as set forth in claim 1, wherein the bonding layer occupies an area of a surface of the metallic terminals inside edges of the metallic terminals.

6. A ceramic heater as set forth in claim 1, wherein the bonding layer contains 40 Wt % of Cu or more.

7. A ceramic heater as set forth in claim 1, wherein at least one of the metallic terminals comprises 70 Wt % of W or more, and the bonding layer contains 40 to 98 Wt % of Cu and 2 to 20 Wt % of Ni.

8. A ceramic heater as set forth in claim 7, wherein the bonding layer contains 60 Wt % of Au or less.

9. A ceramic heater as set forth in claim 8, further comprising an Ni-plated layer formed on one of said metallic terminals, having a thickness of 3 $\mu$m or less, and wherein the outer lead is joined to the Ni-plated layer through the bonding layer.

10. A ceramic heater comprising:

a ceramic rod formed by a lamination of a heater substrates each having formed thereon a heater-patterned layer comprising a heater element and first and second leads connected to the heater element and a covering substrate interposed between the heater substrates;

first and second metallic terminals connected electrically to the first and second leads of the heater-patterned layers of the heater substrates, respectively, said metallic terminals being mounted on surfaces of said ceramic square rod opposed to each other in a direction of lamination of the heater substrates and covering substrate; and outer leads joined to said first and second terminals through at bonding layers made of solder.

11. A ceramic heater as set forth in claim 10, wherein said first metallic terminal is connected to the first leads of the heater substrates through conductive material-coated holes formed in the covering substrate and one of the heater substrates, and the second metallic terminal is connected to the second leads of the heater substrates through conductive material-coated holes formed in the covering substrate and the other heater substrate.

12. A ceramic heater as set forth in claim 10, wherein each of the bonding layers occupies an area of a surface of one of the metallic terminals inside edges of the metallic terminals.

13. A ceramic heater as set forth in claim 10, wherein each of the bonding layers contains 40 Wt % of Cu or more.

14. A ceramic heater as set forth in claim 10, wherein each of the metallic terminals contains 70 Wt % of W or more, and each of the bonding layers contains 40 to 98 Wt % of Cu and 2 to 20 Wt % of Ni.

15. A ceramic heater as set forth in claim 14, wherein each of the bonding layers contains 60 Wt % of Au or less.

16. A ceramic heater as set forth in claim 15, further comprising a Ni-plated layer formed on each of said metallic terminals, having a thickness of 3 $\mu$m or less, and wherein the outer leads are joined to the Ni-plated layers through the bonding layers.

* * * * *